United States Patent
Kamada et al.

(10) Patent No.: US 11,054,382 B2
(45) Date of Patent: Jul. 6, 2021

(54) SENSOR AND METHOD OF MANUFACTURING SENSOR

(71) Applicant: NGK Spark Plug Co., LTD., Nagoya (JP)

(72) Inventors: Kentaro Kamada, Nagoya (JP); Hitoshi Furuta, Nagoya (JP); Satoshi Yamahara, Nagoya (JP)

(73) Assignee: NGK Spark Plug Co., LTD., Nagoya (JP)

( * ) Notice: Subject to any disclaimer, the term of this patent is extended or adjusted under 35 U.S.C. 154(b) by 199 days.

(21) Appl. No.: 16/284,391

(22) Filed: Feb. 25, 2019

(65) Prior Publication Data

US 2019/0277796 A1  Sep. 12, 2019

(30) Foreign Application Priority Data

Mar. 7, 2018 (JP) .............................. JP2018-041118
Dec. 26, 2018 (JP) .............................. JP2018-243194

(51) Int. Cl.
| | |
|---|---|
| *G01N 27/407* | (2006.01) |
| *G01N 33/00* | (2006.01) |
| *G01N 27/406* | (2006.01) |
| *G01N 27/41* | (2006.01) |
| *G01N 27/417* | (2006.01) |
| *G01N 27/409* | (2006.01) |
| *H05B 3/12* | (2006.01) |

(52) U.S. Cl.
CPC ....... *G01N 27/4075* (2013.01); *G01N 27/409* (2013.01); *G01N 27/4067* (2013.01); *G01N 27/41* (2013.01); *G01N 27/417* (2013.01); *G01N 33/0036* (2013.01); *H05B 3/12* (2013.01)

(58) Field of Classification Search
None
See application file for complete search history.

(56) References Cited

U.S. PATENT DOCUMENTS

2009/0188813 A1  7/2009 Kato et al.

FOREIGN PATENT DOCUMENTS

JP  2012-18189 A  1/2012

OTHER PUBLICATIONS

O. Yamamoto, et al. "Platinum-stabilized zirconia composite solid oxide oxygen gas sensor", Sensor and Actuators, B 13(1-3): p. 31-33, May (Year: 1993).*

* cited by examiner

Primary Examiner — J. Christopher Ball
(74) Attorney, Agent, or Firm — Leason Ellis LLP

(57) ABSTRACT

A sensor includes a pump cell and a reference cell generating voltage Vs or current. The pump cell includes a pump cell first electrode and a pump cell second electrode. The surface of the pump cell first electrode includes a noble metal region formed of a noble metal, a ceramic region, and a coexistence region in which the noble metal and the ceramic material coexist. The width of the coexistence region in an A region of the surface of the pump cell first electrode is greater than the width of the coexistence region in a B region of the surface. The A region is a region close to the reference cell first electrode, and the B region is a region located further away from the reference cell first electrode as compared with the A region.

7 Claims, 6 Drawing Sheets

SENSOR AND METHOD OF MANUFACTURING SENSOR

This application claims the benefit of Japanese Patent Applications No. 2018-041118, filed Mar. 7, 2018 and No. 2018-243194, filed Dec. 26, 2018, which are incorporated herein by reference in their entirety.

FIELD OF THE INVENTION

The present disclosure relates to a sensor and to a method of manufacturing a sensor.

BACKGROUND OF THE INVENTION

A conventionally known sensor includes a measurement chamber into which a gas under measurement is introduced, a pump cell, a reference oxygen chamber, and a reference cell. The pump cell pumps out oxygen from the measurement chamber to the outside of the sensor or pumps oxygen into the measurement chamber from the outside. The reference oxygen chamber holds an atmosphere having a predetermined oxygen concentration. The reference cell generates voltage Vs in accordance with the difference in oxygen concentration between the measurement chamber and the reference oxygen chamber.

The pump cell includes a first solid electrolyte body, a first electrode, and a second electrode. The first electrode is formed on the first solid electrolyte body and is exposed to the measurement chamber. The second electrode is formed on the first solid electrolyte body and is exposed to the outside.

The reference cell includes a second solid electrolyte body, a third electrode, and a fourth electrode. The third electrode is formed on the second solid electrolyte body and is exposed to the measurement chamber. The fourth electrode is formed on the second solid electrolyte body and is exposed to the reference oxygen chamber (see Japanese Unexamined Publication No. 2012-18189).

In the above-described sensor, the current Ip flowing through the pump cell is feedback-controlled, for example, such that the voltage Vs of the reference cell becomes constant.

Problems to be Solved by the Invention

The first electrode contains a noble metal and a ceramic material which is the same as the ceramic material contained in the first solid electrolyte body. Rich aging treatment is performed for the first electrode. As a result of the rich aging treatment, the quality alteration of the first electrode progresses, which results in formation of a coexistence region in which the noble metal and the ceramic material coexist. When such a coexistence region is formed, the area of the three-phase interface between the noble metal, the solid electrolyte, and the gas increases. Therefore, the reactivity between the first electrode and the gas is enhanced, thereby enhancing the activity of the first electrode.

In the case of the conventional sensor, in a portion of the first electrode away from the third electrode, quality alteration progresses more easily and activity is higher, as compared with a portion of the first electrode near the third electrode. Therefore, only a portion of the pump cell away from the third electrode mainly pumps out oxygen from the measurement chamber to the outside and pumps oxygen into the measurement chamber from the outside. As a result, the responsiveness of the pump cell to changes in the voltage Vs is low.

The object of one aspect of the present disclosure is to provide a sensor whose pump cell is high in responsiveness to changes in the voltage Vs or current generated by the reference cell and to provide a method of manufacturing the sensor.

SUMMARY OF THE INVENTION

Means for Solving the Problems

A first aspect of the present disclosure is a sensor comprising a detection section. The detection section includes a measurement chamber into which a gas under measurement is introduced, a pump cell which pumps out oxygen from the measurement chamber to an element external space or pumps oxygen into the measurement chamber from the element external space, and a reference cell which generates voltage Vs or current in accordance with the difference in oxygen concentration between the measurement chamber and a reference space which holds an atmosphere having a predetermined oxygen concentration.

The pump cell includes a pump cell solid electrolyte body containing a ceramic material, a porous pump cell first electrode formed on the pump cell solid electrolyte body and exposed to the measurement chamber, and a pump cell second electrode formed on the pump cell solid electrolyte body and exposed to the element external space or a space communicating with the element external space. The reference cell includes a reference cell solid electrolyte body, a reference cell first electrode formed on the reference cell solid electrolyte body and exposed to the measurement chamber, and a reference cell second electrode formed on the reference cell solid electrolyte body and exposed to the reference space. The pump cell first electrode contains a noble metal and a ceramic material which is the same type of material as the ceramic material contained in the pump cell solid electrolyte body. When a surface of the pump cell first electrode is observed with magnification, the surface, which is exposed to the measurement chamber, includes a noble metal region formed of the noble metal, a ceramic region formed of the ceramic material, and a coexistence region where the noble metal and the ceramic material coexist. The coexistence region in an A region of the surface which is defined below has a width greater than that of the coexistence region in a B region of the surface which is defined below.

The A region: A portion of the surface farthest from the reference cell first electrode is defined as a farthest portion. A portion of the surface closest to the reference cell first electrode is defined as a closest portion. The distance between the farthest portion and the closest portion is denoted by L. A position on the surface which is offset from the closest portion toward the farthest portion by L/6 is defined as an a-point. The region within a circle whose center is located at the a-point and whose radius is L/12 is defined as the A region.

The B region: A position on the surface which is offset from the farthest portion toward the closest portion by L/6 is defined as a b-point. The region within a circle whose center is located at the b-point and whose radius is L/12 is defined as the B region.

In the sensor of the first aspect of the present disclosure, a portion of the pump cell first electrode close to the reference cell first electrode has an expanded coexistence region as a result of a greater degree of progress in quality alteration, as compared with a portion of the pump cell first electrode away from the reference cell first electrode. Therefore, a portion of the pump cell close to the reference cell first electrode mainly pumps out oxygen from the measurement chamber to the element external space and pumps oxygen into the measurement chamber from the element external space. As a result, the pump cell has high responsiveness to changes in the voltage Vs or current generated by the reference cell.

A second aspect of the present disclosure is a method of manufacturing a sensor comprising a detection section. The detection section includes a measurement chamber into which a gas under measurement is introduced, a pump cell which pumps out oxygen from the measurement chamber to an element external space or pumps oxygen into the measurement chamber from the element external space, and a reference cell which generates voltage Vs or current in accordance with the difference in oxygen concentration between the measurement chamber and a reference space which holds an atmosphere having a predetermined oxygen concentration.

The pump cell includes a pump cell solid electrolyte body, a porous pump cell first electrode formed on the pump cell solid electrolyte body and exposed to the measurement chamber, and a pump cell second electrode formed on the pump cell solid electrolyte body and exposed to the element external space or a space communicating with the element external space. The reference cell includes a reference cell solid electrolyte body, a reference cell first electrode formed on the reference cell solid electrolyte body and exposed to the measurement chamber, and a reference cell second electrode formed on the reference cell solid electrolyte body and exposed to the reference space.

In the sensor manufacturing method of the second aspect of the present disclosure, rich aging treatment is performed for the pump cell first electrode such that a temperature of the pump cell first electrode in an A region of a surface of the pump cell first electrode, which is defined below, becomes higher than a temperature of the pump cell first electrode in a B region of the surface which is defined below.

The A region: A portion of the surface farthest from the reference cell first electrode is defined as a farthest portion. A portion of the surface closest to the reference cell first electrode is defined as a closest portion. The distance between the farthest portion and the closest portion is denoted by L. A position on the surface which is offset from the closest portion toward the farthest portion by L/6 is defined as an a-point. The region within a circle whose center is located at the a-point and whose radius is L/12 is defined as the A region.

The B region: A position on the surface which is offset from the farthest portion toward the closest portion by L/6 is defined as a b-point. The region within a circle whose center is located at the b-point and whose radius is L/12 is defined as the B region.

In the sensor manufactured by the sensor manufacturing method of the second aspect of the present disclosure, a portion of the pump cell first electrode close to the reference cell first electrode has an expanded coexistence region as a result of a greater degree of progress in quality alteration, as compared with a portion of the pump cell first electrode away from the reference cell first electrode. Therefore, a portion of the pump cell close to the reference cell first electrode mainly pumps out oxygen from the measurement chamber to the element external space and pumps oxygen into the measurement chamber from the element external space. As a result, the pump cell has high responsiveness to changes in the voltage Vs or current generated by the reference cell.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An exemplary embodiment of the present disclosure will be described with reference to the drawings.

First Embodiment

1. Overall Structure of NOx Sensor 1

The overall structure of an NOx sensor 1 will be described with reference to FIGS. 1 and 2. Notably, in the following description, the lower side in FIG. 1 is called the forward end side of the NOx sensor 1, and the upper side in FIG. 1 is called the rear end side of the NOx sensor 1.

Figure 1:
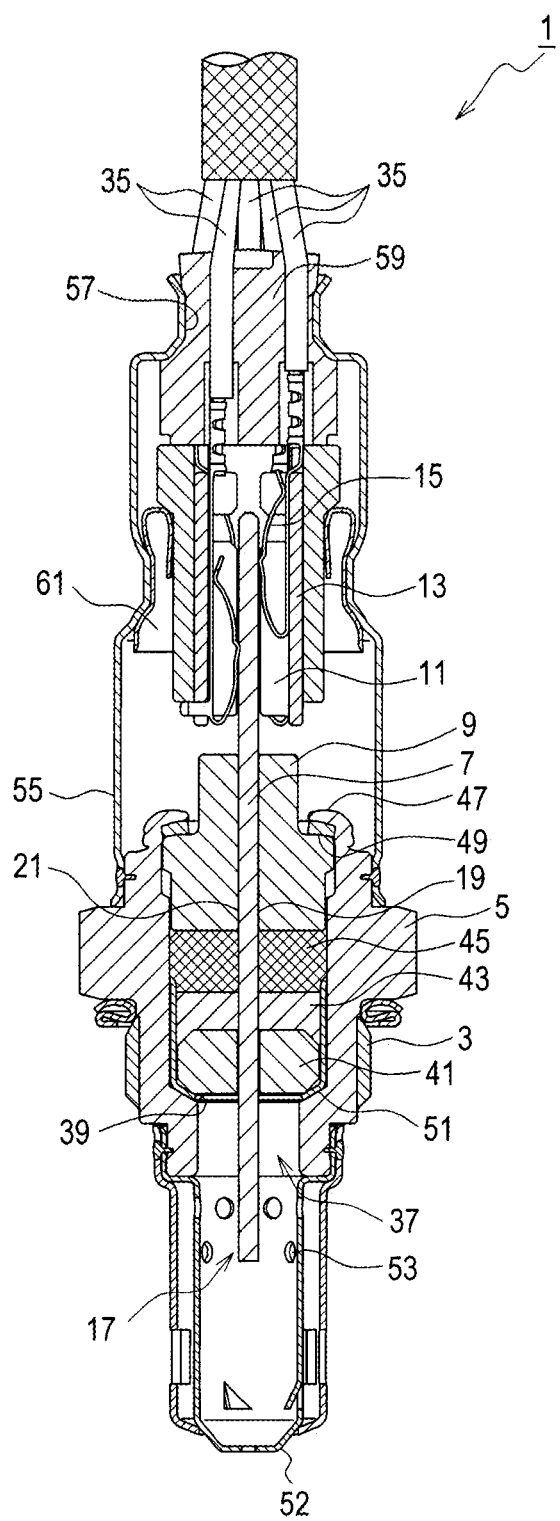
FIG. 1 is a sectional view of an NOx sensor taken along its axial direction.

As shown in FIG. 1, the NOx sensor 1 includes a metallic shell 5, a gas sensor element 7, a ceramic sleeve 9, an insulating separator 13, and six lead frames 15. Notably, in FIG. 1, only some of the six lead frames 15 are illustrated.

These components will now be described. As shown in FIGS. 1 and 2, the gas sensor element 7 is a plate-shaped laminate extending in the axial direction. The gas sensor element 7 extends through the metallic shell 5. A forward end portion of the gas sensor element 7 is to be exposed to exhaust gas to be measured. The exhaust gas corresponds to the gas under measurement appearing in the claims. A detection section 17 is formed at the forward end of the gas sensor element 7. The detection section 17 is covered with an unillustrated protection layer.

Figure 2:
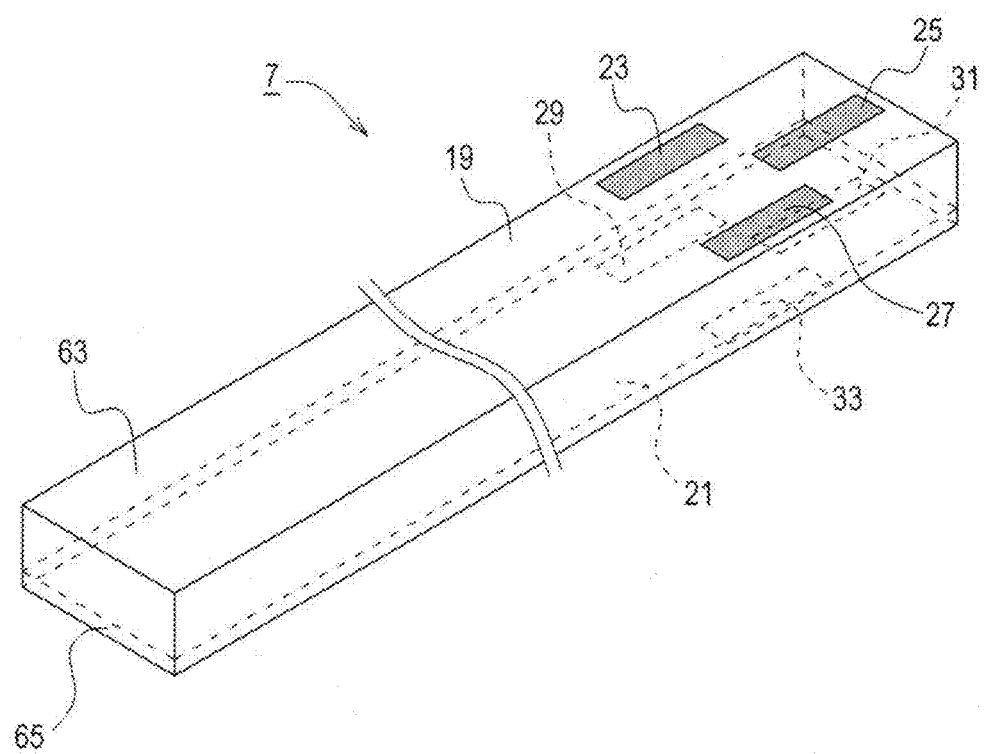
FIG. 2 is a perspective view of a gas sensor element with its portion in the axial direction removed.

As shown in FIG. 2, electrode pads 23, 25, 27, 29, 31, and 33 are formed on a rear end portion of the gas sensor element 7. The electrode pads 23, 25, and 27 are formed on a first main face 19 which is one of outer surfaces of the gas sensor element 7 located on one side in the thickness direction. The electrode pads 29, 31, and 33 are formed on a second main face 21 which is another of the outer surfaces of the gas sensor element 7 located opposite the first main face 19.

The ceramic sleeve 9 has a tubular shape. The ceramic sleeve 9 is disposed to surround the circumference of the gas sensor element 7.

The insulating separator 13 is formed of, for example, an alumina insulating material. The insulating separator 13 has an element insertion hole 11 extending therethrough in the axial direction. The wall surface of the element insertion hole 11 at least partially surrounds the gas sensor element 7 and the lead frames 15.

Since the lead frames 15 and the gas sensor element 7 are held in the element insertion hole 11 by the insulating separator 13, the lead frames 15 are electrically connected to the electrode pads 23 to 33, respectively, of the gas sensor element 7.

The lead frames 15 are also electrically connected to lead wires 35 disposed to extend from the outside of the sensor to the interior of the sensor. The lead frames 15 form current paths for currents which flow between the electrode pads 23 to 33 and an external device to which the lead wires 35 are connected.

The metallic shell 5 is a generally tubular metallic member formed of, for example, stainless steel. The metallic shell 5 has a through hole 37 extending therethrough in the axial direction, and has a ledge portion 39 which protrudes radially inward in the through hole 37. A screw portion 3 used to fix the NOx sensor 1 to an exhaust pipe is formed on the outer surface of the metallic shell 5.

The metallic shell 5 is configured to hold the gas sensor element 7 inserted into the through hole 37. The gas sensor element 7 is held such that the detection section 17 is exposed to the outside on the forward end side of the through hole 37 and the electrode pads 23 to 33 are exposed to the outside on the rear end side of the through hole 37.

Within the through hole 37, an annular ceramic holder 41, powder-charged layers (talc rings) 43 and 45, and the above-described ceramic sleeve 9 are stacked in this order from the forward end side toward the rear end side so as to surround the circumference of the gas sensor element 7.

A crimp ring 49 is disposed between the ceramic sleeve 9 and a rear end portion 47 of the metallic shell 5. A metal cup 51 is disposed between the ceramic holder 41 and the ledge portion 39 of the metallic shell 5. Notably, the rear end portion 47 is crimped to press the ceramic sleeve 9 toward the forward end side via the crimp ring 49.

A tubular protector 52 formed of, for example, stainless steel is disposed on the forward end side of the metallic shell 5 so as to cover a forward end portion of the gas sensor element 7. The protector 52 has gas passage holes 53 which allows passage of exhaust gas therethrough. The protector 52 has a double structure; i.e., is composed of an inner protector and an outer protector.

An outer tube 55 formed of, for example, stainless steel is fixed to a rear end portion of the metallic shell 5. An opening 57 at the rear end of the outer tube 55 is closed by a grommet 59 formed of, for example, fluororubber.

Notably, the insulating separator 13 is held inside the outer tube 55 such that its rear end is in contact with the grommet 59. The holding of the insulating separator 13 is performed by a holding member 61. The holding member 61 is disposed inside the outer tube 55 and is fixed thereto by means of crimping.

2. Structure of Gas Sensor Element 7

The structure of the gas sensor element 7 will be described with reference to FIGS. 2 to 8. As shown in FIG. 2, the gas sensor element 7 has the shape of a plate having a rectangular transverse section. The gas sensor element 7 is composed of an element section 63 and a heater 65 stacked together. Each of the element section 63 and the heater 65 is formed into the shape of a plate extending in the axial direction. The element section 63 corresponds to the detection section appearing in the claims.

Figure 3:
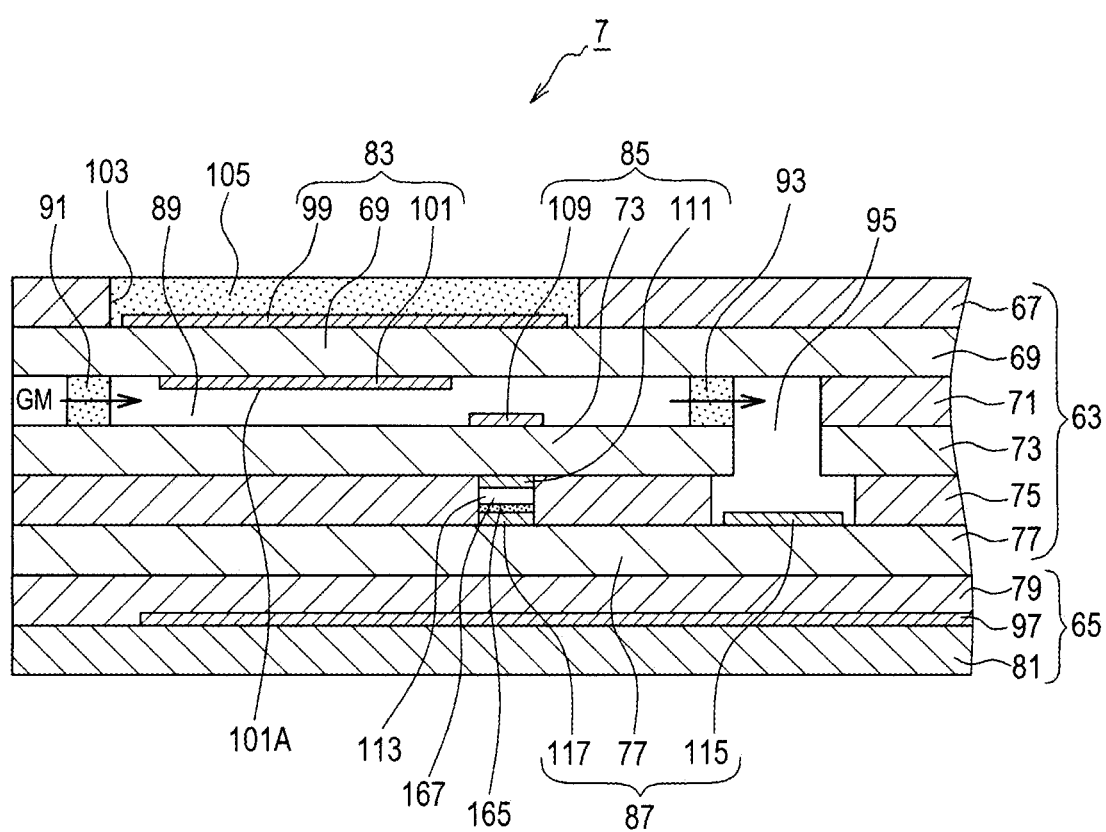
FIG. 3 is an enlarged thicknesswise sectional view of a forward end portion of the gas sensor element for showing the internal structure of the forward end portion.

FIG. 3 shows the structure of a forward end portion of the gas sensor element 7. The gas sensor element 7 has a multi-layer structure in which an insulating layer 67, a first solid electrolyte body 69, an insulating layer 71, a second solid electrolyte body 73, an insulating layer 75, a third solid electrolyte body 77, and insulating layers 79 and 81 are arranged in this order from the upper side in FIG. 3. The insulating layer 67, the first solid electrolyte body 69, the insulating layer 71, the second solid electrolyte body 73, the insulating layer 75, and the third solid electrolyte body 77 correspond to the element section 63. The gas sensor element 7 includes a first pump cell 83, a reference cell 85, and a second pump cell 87.

A first measurement chamber 89 is formed between the first solid electrolyte body 69 and the second solid electrolyte body 73. The left end of the first measurement chamber 89 in FIG. 3 is an inlet. A first diffusion resistor portion 91 is disposed in this inlet. The exhaust gas GM is introduced into the first measurement chamber 89 from the element external space through the first diffusion resistor portion 91. A second diffusion resistor portion 93 is disposed at the end of the first measurement chamber 89 opposite the inlet. The element external space means the outside of the gas sensor element 7.

In FIG. 3, a second measurement chamber 95 is formed on the right side of the second diffusion resistor portion 93. The second measurement chamber 95 communicates with the first measurement chamber 89 through the second diffusion resistor portion 93. The second measurement chamber 95 is formed between the first solid electrolyte body 69 and the third solid electrolyte body 77. A portion of the second solid electrolyte body 73 corresponding to the second measurement chamber 95 is removed.

Each of the first to third solid electrolyte bodies 69, 73, and 77 contains, as a main component, zirconia having oxygen ion conductivity. Each of the insulating layers 67, 71, 75, 79, and 81 contains alumina as a main component. Each of the first and second diffusion resistor portions 91 and 93 is formed of a porous substance such as alumina. Notably, the main component of a ceramic layer means a component which is contained in the ceramic layer in an amount of 50 mass % or more.

A resistance heating element 97 is embedded between the insulating layers 79 and 81. The resistance heating element 97 extends in the left-right direction in FIG. 3. The resistance heating element 97 is formed of, for example, platinum. The insulating layers 79 and 81 and the resistance heating element 97 form the heater 65. The heater 65 is in contact with the element section 63. The heater 65 heats the gas sensor element 7 to a predetermined activation temperature, thereby enhancing the oxygen-ion conductivities of the first to third solid electrolyte bodies 69, 73, and 77 for stable operation. The resistance heating element 97 corresponds to the heating element appearing in the claims. The insulating layers 79 and 81 and the resistance heating element 97 correspond to the heating section appearing in the claims.

The first pump cell 83 includes the first solid electrolyte body 69, a first electrode 101, and a second electrode 99. The first electrode 101 and the second electrode 99 sandwich the first solid electrolyte body 69 therebetween.

The first electrode 101 is formed on the first solid electrolyte body 69. The first electrode 101 is exposed to the first measurement chamber 89. The first electrode 101 is porous. The first electrode 101 contains platinum, zirconia, and an alloy of platinum and zirconium (hereinafter referred to as "PtZr alloy"). The volume ratio of the PtZr alloy in the first electrode 101 is 15 vol % or more. Zirconia corresponds to the ceramic material contained in the first solid electrolyte body 69. Platinum corresponds to the noble metal appearing in the claims. The first solid electrolyte body 69 corresponds to the pump cell solid electrolyte body appearing in the claims. The first electrode 101 corresponds to the pump cell first electrode appearing in the claims. The second electrode 99 corresponds to the pump cell second electrode appearing in the claims.

Figure 4:
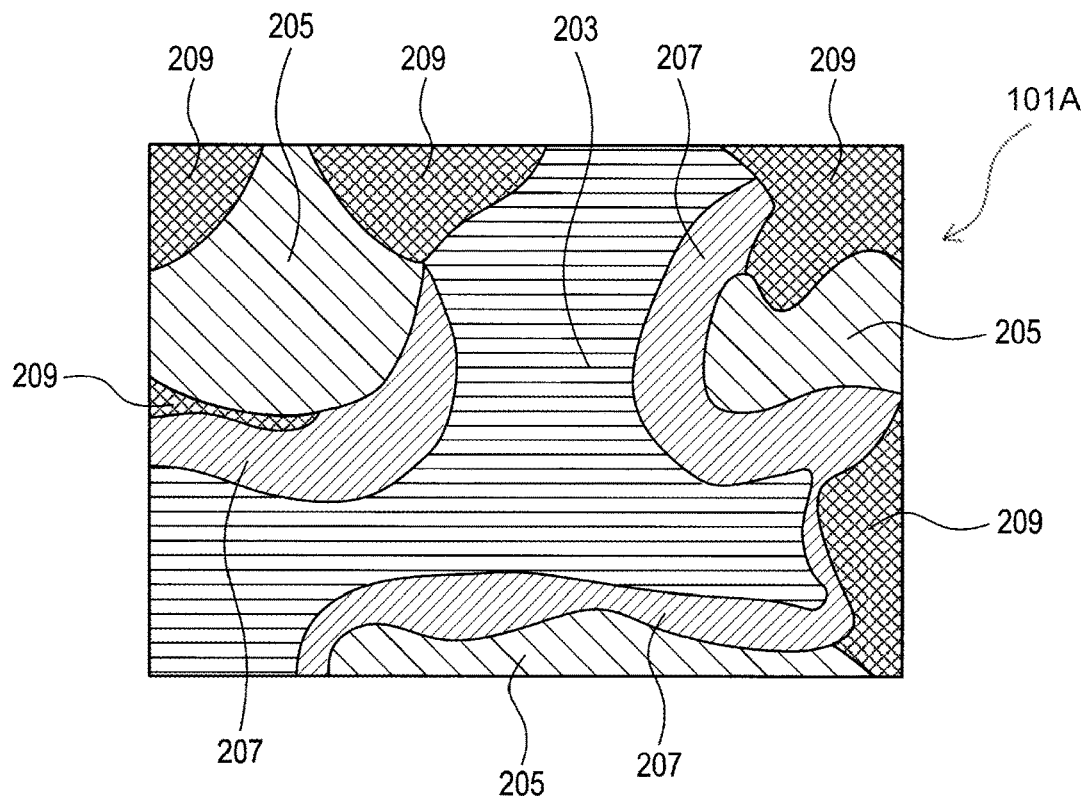
FIG. 4 is an explanatory view showing zirconia regions, platinum regions, coexistence regions, and gap regions on the surface of a first electrode.

A surface of the first electrode 101 exposed to the first measurement chamber 89 will be referred to as a surface 101A. When the surface 101A is observed with magnification, for example, as shown in FIG. 4, zirconia regions 203 formed of zirconia, platinum regions 205 formed of platinum, coexistence regions 207 formed of platinum, zirconia, and PtZr alloy, and gap regions 209 are present. Notably, each region can be identified through XRD analysis. The platinum regions 205 correspond to the noble metal region appearing in the claims. The zirconia regions 203 correspond to the ceramic region appearing in the claims. The coexistence regions 207 are regions where the noble metal and the ceramic material coexist.

The second electrode 99 is formed on the first solid electrolyte body 69. The second electrode 99 is exposed to the element external space. The second electrode 99 contains platinum as a main component. The second electrode 99 is covered with a porous layer 105. The porous layer 105 is embedded in an opening 103 of the insulating layer 67. The porous layer 105 is formed of a porous material which allows passage of gas (oxygen, etc.) therethrough. An example of the porous material is alumina.

The reference cell 85 includes the second solid electrolyte body 73, a third electrode 109, and a fourth electrode 111. The third electrode 109 is formed on the second solid electrolyte body 73. The fourth electrode 111 is formed on the second solid electrolyte body 73. The third electrode 109 and the fourth electrode 111 sandwich the second solid electrolyte body 73 therebetween. The third electrode 109 is exposed to the first measurement chamber 89.

When viewed in the stacking direction, the third electrode 109 is located at a position which does not overlap with the first electrode 101. Also, as viewed in the flow direction of the exhaust gas introduced from the inlet of the first measurement chamber 89, the third electrode 109 is located on the downstream side of the first electrode 101.

The fourth electrode 111 is exposed to a reference oxygen chamber 113, which will be described later. Each of the third electrode 109 and the fourth electrode 111 contains platinum as a main component. The second solid electrolyte body 73 corresponds to the reference cell solid electrolyte body appearing in the claims. The third electrode 109 corresponds to the reference cell first electrode appearing in the claims. The fourth electrode 111 corresponds to the reference cell second electrode appearing in the claims. In the first embodiment, the pump cell solid electrolyte body and the reference cell solid electrolyte body are separate bodies. In the first embodiment, the pump cell second electrode and the reference cell second electrode are separate electrodes.

The reference oxygen chamber 113 is a space formed by removing a portion of the insulating layer 75. The reference oxygen chamber 113 is a space surrounded by the second solid electrolyte body 73, the third solid electrolyte body 77, and the insulating layer 75. The reference oxygen chamber 113 holds therein an atmosphere having a predetermined oxygen concentration. The reference oxygen chamber 113 corresponds to the reference space appearing in the claims and holding an atmosphere having a predetermined oxygen concentration. In the first embodiment, the space communicating with the element external space and the reference space which holds an atmosphere having a predetermined oxygen concentration are different spaces.

The second pump cell 87 includes the third solid electrolyte body 77, a fifth electrode 115, and a sixth electrode 117. The fifth electrode 115 and the sixth electrode 117 are formed on one surface of the third solid electrolyte body 77. The fifth electrode 115 is exposed to the second measurement chamber 95. The sixth electrode 117 is exposed to the reference oxygen chamber 113. The fifth electrode 115 and the sixth electrode 117 are separated from each other by the insulating layer 75. Each of the fifth electrode 115 and the sixth electrode 117 contains platinum as a main component. The sixth electrode 117 is covered with an insulating protection layer 165 formed of a porous material. A gap 167, which is a hollow space, is present in the reference oxygen chamber 113.

Figure 5:
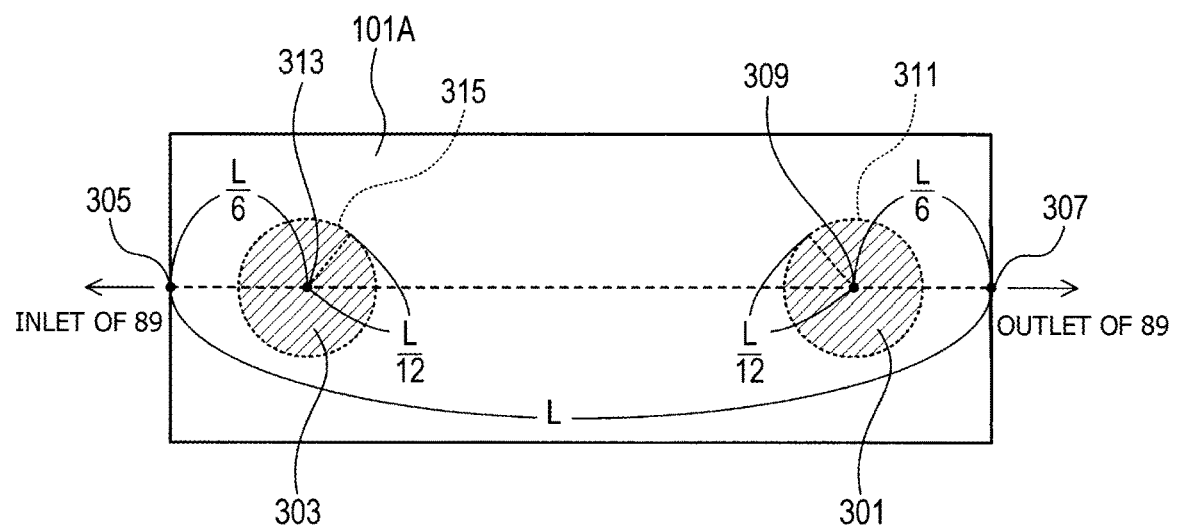
FIG. 5 is an explanatory view showing an A region and a B region on the surface of the first electrode.

FIG. 5 shows the surface 101A as viewed from the second solid electrolyte body 73. The left-hand side in FIG. 5 corresponds to the inlet side of the first measurement chamber 89. The right-hand side in FIG. 5 corresponds to the outlet side of the first measurement chamber 89. An "A" region 301 and a "B" region 303 are defined on the surface 101A as follows.

A region 301: A portion of the surface 101A farthest from the third electrode 109 is defined as a farthest portion 305. A portion of the surface 101A closest to the third electrode 109 is defined as a closest portion 307. The distance between the farthest portion 305 and the closest portion 307 is denoted by L. A position on the surface 101A which is offset from the closest portion 307 toward the farthest portion 305 by L/6 is defined as an a-point 309. The region within a circle 311 whose center is located at the a-point 309 and whose radius is L/12 is defined as the A region 301.

B region 303: A position on the surface 101A which is offset from the farthest portion 305 toward the closest portion 307 by L/6 is defined as a b-point 313. The region within a circle 315 whose center is located at the b-point 313 and whose radius is L/12 is defined as the B region 303.

Figure 7:
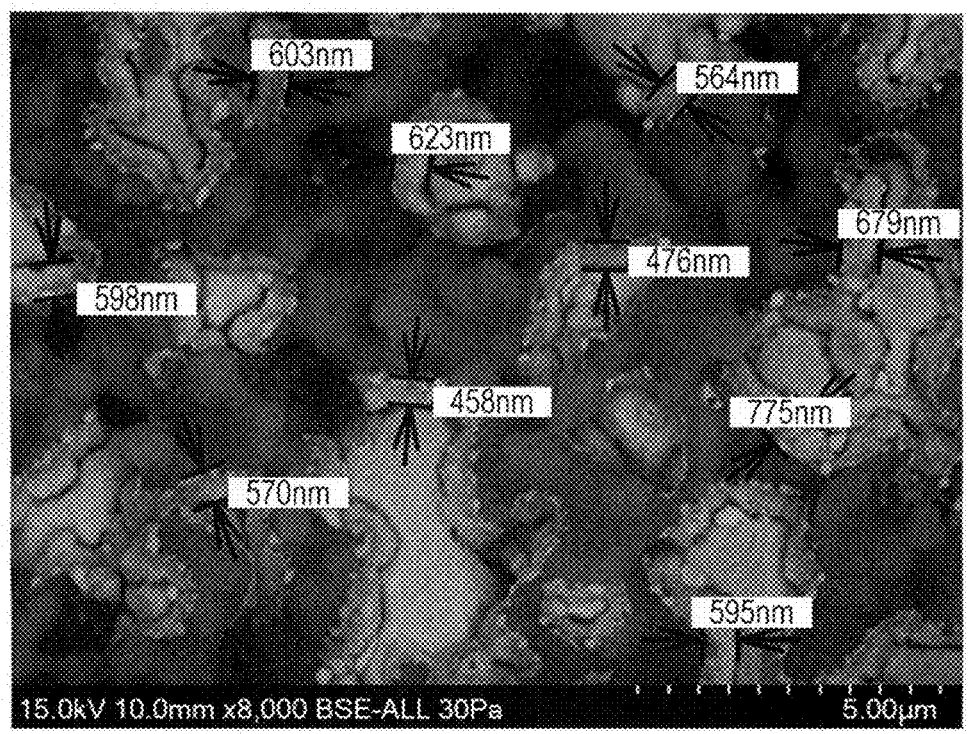
FIG. 7 is a photograph showing a backscattered electron image obtained in the A region and coexistence region widths measured at 10 locations in the backscattered electron image.
Figure 8:
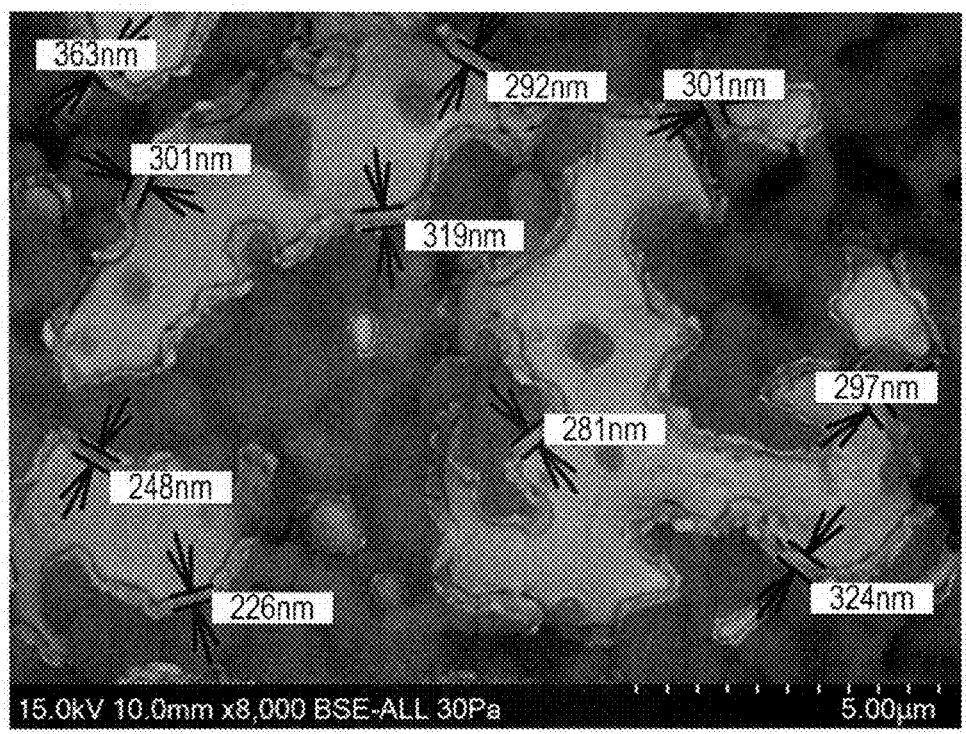
FIG. 8 is a photograph showing a backscattered electron image obtained in the B region and coexistence region widths measured at 10 locations in the backscattered electron image.

The width W of each coexistence region 207 in the A region 301 is greater than the width W of each coexistence region 207 in the B region 303. Notably, the width W of each coexistence region 207 is calculated as follows. The surface 101A is observed with magnification so as to obtain a backscattered electron image having a magnification of 8000×. At randomly selected ten locations of the coexistence regions 207 on the backscattered electron image, the width of each coexistence region 207 (hereinafter referred to as the "local width") is measured. FIG. 7 shows the backscattered electron image obtained at the A region 301 and the local widths of the coexistence regions 207 measured at the ten locations in the backscattered electron image. FIG. 8 shows the backscattered electron image obtained at the B region 303 and the local widths of the coexistence regions 207 measured at the ten locations in the backscattered electron image. The average of the local widths of the coexistence regions 207 measured at the ten locations is used as the width W of the coexistence regions 207.

The reason why the width W of the coexistence regions 207 in the A region 301 is greater than the width W of the coexistence regions 207 in the B region 303 is that in a portion of the first electrode 101 close to the third electrode 109, the coexistence regions 207 have expanded areas because of progress of quality alteration, as compared with a portion of the first electrode 101 away from the third electrode 109.

In the portion of the first electrode 101 close to the third electrode 109, its quality alteration has progressed further and the coexistence regions 207 have expanded more as compared with the portion of the first electrode 101 away from the third electrode 109. Therefore, a portion of the first pump cell 83 close to the third electrode 109 mainly pumps out oxygen from the first measurement chamber 89 to the element external space and pumps oxygen into the first measurement chamber 89 from the element external space. As a result, the first pump cell 83 has high responsiveness to changes in the voltage Vs.

The ratio of the width W of the coexistence regions 207 in the A region 301 to the width W of the coexistence regions 207 in the B region 303 (hereinafter referred to as the "A/B width ratio") is preferably 1.1 or greater, more preferably 1.3 or greater, and particularly preferably 1.5 or greater. In the case where the A/B width ratio is 1.1 or greater, the responsiveness of the first pump cell 83 to changes in the voltage Vs is higher. In the case where the A/B width ratio is 1.3 or greater, the responsiveness of the first pump cell 83 to changes in the voltage Vs is even higher. In the case where the A/B width ratio is 1.5 or greater, the responsiveness of the first pump cell 83 to changes in the voltage Vs is particularly high.

3. Configuration of sensor controller 169

Figure 6:
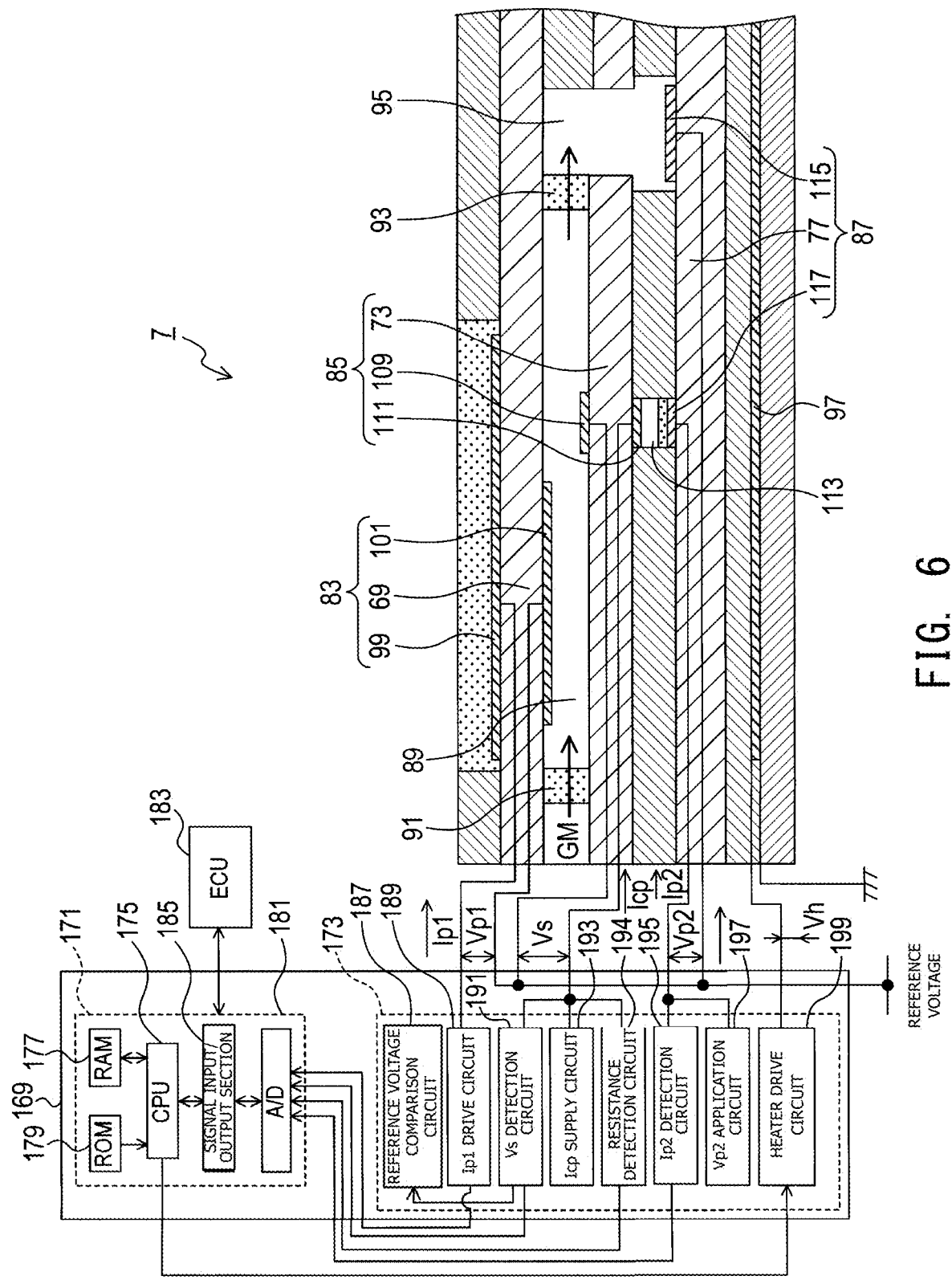
FIG. 6 is a block diagram showing an electrical configuration of a sensor controller connected to the gas sensor element.

The configuration of a sensor controller 169 which controls operation of the gas sensor element 7 will be described with reference to FIG. 6. The sensor controller 169 includes a microcomputer 171, an electric circuit section 173, etc. The microcomputer 171 includes a CPU 175 which executes various types of computations, a RAM 177 which stores computation results, etc., and a ROM 179 which stores programs executed by the CPU 175, etc.

The microcomputer 171 further includes an A/D converter 181, a signal input/output section 185, an unillustrated timer clock, etc. The signal input/output section 185 is connected to the electric circuit section 173 through the A/D converter 181 and communicates with an ECU 183.

The electric circuit section 173 is composed of a reference voltage comparison circuit 187, an Ip1 drive circuit 189, a Vs detection circuit 191, an Icp supply circuit 193, a resistance detection circuit 194, an Ip2 detection circuit 195, a Vp2 application circuit 197, and a heater drive circuit 199. Under the control by the microcomputer 171, the electric circuit section 173 determines the concentration of NOx in the exhaust gas GM by using the gas sensor element 7.

The first electrode 101, the third electrode 109, and the fifth electrode 115 are connected to a reference potential. One electrode of the resistance heating element 97 is grounded.

4. NOx Concentration Determination Process

A process of determining the concentration of NOx in the exhaust gas GM, which is executed by the sensor controller 169 and the NOx sensor 1, will be described. The heater drive circuit 199 supplies drive current to the resistance heating element 97. The resistance heating element 97 increases its temperature so as to heat the first to third solid electrolyte bodies 69, 73, and 77 for activation. As a result, the first pump cell 83, the reference cell 85, and the second pump cell 87 start their operations.

The exhaust gas GM is introduced into the first measurement chamber 89 while the introduction of the exhaust gas GM is restricted by the first diffusion resistor portion 91. The Icp supply circuit 193 supplies a weak current Icp to the reference cell 85 to flow from the fourth electrode 111 to the third electrode 109. Therefore, oxygen in the exhaust gas GM can receive electrons from the third electrode 109 located in the first measurement chamber 89 and serving as a negative electrode and becomes oxygen ions. The oxygen ions flow through the second solid electrolyte body 73 and moves into the reference oxygen chamber 113. Namely, as a result of the flow of the current Icp between the third electrode 109 and the fourth electrode 111, oxygen in the first measurement chamber 89 is fed into the reference oxygen chamber 113.

The Vs detection circuit 191 detects the voltage Vs between the third electrode 109 and the fourth electrode 111. The voltage Vs corresponds to the difference between the oxygen concentration in the first measurement chamber 89 and the oxygen concentration in the reference oxygen chamber 113. The reference voltage comparison circuit 187 compares the voltage Vs detected by the Vs detection circuit 191 and a reference voltage (425 mV) and outputs the comparison results to the Ip1 drive circuit 189. The oxygen concentration in the first measurement chamber 89 is adjusted such that the voltage Vs is maintained at about 425 mV, whereby the oxygen concentration in the exhaust gas GM within the first measurement chamber 89 approaches a predetermined concentration (for example, $10^{-8}$ to $10^{-9}$ atm).

When the oxygen concentration of the exhaust gas GM introduced into the first measurement chamber 89 is lower than the predetermined concentration, the Ip1 drive circuit 189 supplies the current Ip1 to the first pump cell 83 such that the second electrode 99 serves as a negative electrode, whereby oxygen is pumped into the first measurement chamber 89 from the element external space. Meanwhile, when the oxygen concentration of the exhaust gas GM introduced into the first measurement chamber 89 is higher than the predetermined concentration, the Ip1 drive circuit 189 supplies the current Ip1 to the first pump cell 83 such that the first electrode 101 serves as a negative electrode, whereby oxygen is pumped out from the first measurement chamber 89 to the element external space.

The exhaust gas GM whose oxygen concentration has been adjusted in the first measurement chamber 89 is introduced into the second measurement chamber 95 through the second diffusion resistor portion 93. NOx contained in the exhaust gas GM having come into contact with the fifth electrode 115 within the second measurement chamber 95 is decomposed to $N_2$ and $O_2$ on the fifth electrode 115 as a result of application of a voltage Vp2 between the sixth electrode 117 and the fifth electrode 115 by the Vp2 application circuit 197. Oxygen produced as a result of the decomposition flows, in the form of oxygen ions, through the third solid electrolyte body 77 and moves into the reference oxygen chamber 113. As a result, the current flowing through the second pump cell 87 assumes a value corresponding to the concentration of NOx.

The sensor controller 169 measures the current Ip2 flowing through the second pump cell 87 by using the Ip2 detection circuit 195 and determines the NOx concentration in the exhaust gas GM from the current Ip2. Specifically, the relation between the NOx concentration and the current Ip2 is obtained in advance, and a map or the like which represents the relation is prepared. The sensor controller 169 determines the NOx concentration from the measured current Ip2 by referring to the map or the like.

5. Method of Manufacturing NOx Sensor 1

A method of manufacturing the NOx sensor 1 will be described.

(5-1) Method of Manufacturing Gas Sensor Element 7

Ceramic sheets which are the materials of the insulating layer 67, the first solid electrolyte body 69, the second solid electrolyte body 73, the third solid electrolyte body 77, and the insulating layers 79 and 81 are prepared. Through holes, etc. are formed in each ceramic sheet as appropriate. Also, the insulating layer 71 and 75 are formed on the corresponding ceramic sheets by screen printing.

Next, in order to form the electrodes 99, 101, 109, 111, 115, and 117, pastes containing the materials of the electrodes are applied to the surfaces of the corresponding ceramic sheets. The paste for forming the first electrode 101 contains platinum and $ZrO_2$. The paste for forming other electrodes contains platinum as a main component.

Next, the ceramic sheets are stacked together so as to form a laminate, and the laminate is fired. At that time, a first electrode precursor is formed in a region where the first electrode 101 is to be formed. The first electrode precursor contains platinum and $ZrO_2$. When the mass of platinum contained in the first electrode precursor is 100 parts by mass, the mass of $ZrO_2$ contained in the first electrode precursor is 22 parts by mass. Also, in the first electrode precursor, the volume occupied by platinum is 56% by volume, and the volume occupied by $ZrO_2$ is 44% by volume.

Next, rich aging treatment is performed for the first electrode precursor. The conditions of the rich aging treatment are, for example as follows.

The atmosphere of the first electrode precursor: rich atmosphere

The voltage between the first electrode precursor and the second electrode 99: 0.7 to 0.8 V The time of the rich aging treatment: 40 to 50 sec The rich atmosphere means an atmosphere whose oxygen proportion is smaller than that of an atmosphere whose air-fuel ratio is the stoichiometric air-fuel ratio ($\lambda=1$). The stoichiometric air-fuel ratio is the mixing ratio of air and fuel which allows ideal complete combustion.

In the rich aging treatment, the first electrode precursor is heated by using a heater. The heater used may be the heater 65 or an external heater.

In the rich aging treatment, the temperature of the first electrode precursor in the A region 301 is higher than the temperature of the first electrode precursor in the B region 303. Such a temperature difference can be realized by a method of rendering the power of a portion of the heater on the closest portion 307 side larger than the power of a portion of the heater on the farthest portion 305 side. Specifically, the portion of the heater on the closest portion 307 side is made thinner than the portion of the heater on the farthest portion 305 side. The temperature of the first electrode precursor was measured by using an infrared radiation thermometer of CHINO Corporation.

An alternative method of realizing the above-mentioned temperature difference is jetting a low temperature gas to a portion of the heater on the farthest portion 305 side, thereby cooling that portion.

Alternatively, the following method is employed so as to realize the above-mentioned temperature difference. The heater and the first electrode precursor are placed in a chamber. The distance from the inner wall of the chamber to the first electrode precursor is set such that the distance is large on the farthest portion 305 side and is small on the closest portion 307 side. In this case, the amount of radiation heat received by the first electrode precursor from the inner wall of the chamber is small on the farthest portion 305 side and is large on the closest portion 307 side. As a result, the above-mentioned temperature difference can be realized.

As a result of the rich aging treatment, the quality alteration of the first electrode precursor progresses and the coexistence regions 207 are produced. As a result, the first electrode 101 is formed from the first electrode precursor, whereby the gas sensor element 7 is completed. Since the temperature of the first electrode precursor in the A region 301 is higher than the temperature of the first electrode precursor in the B region 303, the width W of the coexistence regions 207 in the A region 301 is greater than the width W of the coexistence regions 207 in the B region 303.

The greater the difference between the temperature of the first electrode precursor in the A region and the temperature of the first electrode precursor in the B region (hereinafter referred to as the "A-B temperature difference"), the greater the A/B width ratio. By making the A-B temperature difference sufficiently large, the A/B width ratio can be made equal to or greater than 1, or equal to greater than 1.1, or equal to or greater than 1.3, or equal to or greater than 1.5.

(5-2) Method of Manufacturing Other Components

Components of the NOx sensor 1 other than the gas sensor element 7 can be manufactured by publicly known methods.

6. Evaluation of NOx Sensor 1

The NOx sensor 1 was manufactured by the method described in the section entitled "5. Method of manufacturing NOx sensor 1." The conditions of the rich aging treatment for the first electrode precursor were as follows.

The atmosphere of the first electrode precursor in the rich aging treatment: $H_2$=2.35 vol. %, $H_2O$=10 vol. %, $N_2$=balance The flow rate of the atmosphere gas in the rich aging treatment: 7 L/min The voltage between the first electrode precursor and the second electrode 99 in the rich aging treatment: 0.77 V The time of the rich aging treatment: 40 sec At the time of the rich aging treatment, the temperature of the first electrode precursor in the A region 301 was rendered higher than the temperature of the first electrode precursor in the B region 303 by the method of making the portion of the heater on the closest portion 307 side thinner than the portion of the heater on the farthest portion 305 side.

In the manufactured NOx sensor 1, the width W of the coexistence regions 207 in the A region 301 and the width W of the coexistence regions 207 in the B region 303 were measured. Table 1 shows the measurement results. Notably, Table 1 also shows the measured values of the local widths at ten locations used for calculation of each width W.

TABLE 1

|  | A region | B region |
|---|---|---|
| Width W (nm) | 594.1 | 295.2 |
| Local widths at 10 locations (nm) | 595 | 363 |
|  | 775 | 301 |
|  | 679 | 248 |
|  | 476 | 226 |
|  | 564 | 319 |
|  | 623 | 292 |
|  | 458 | 281 |

TABLE 1-continued

| A region | B region |
|---|---|
| 570 | 301 |
| 598 | 297 |
| 603 | 324 |

7. Effects Achieved by NOx Sensor 1

(1A) In the NOx sensor 1, a portion of the first electrode 101 close to the third electrode 109 has expanded coexistence regions 207 as a result of a greater degree of progress in quality alteration, as compared with a portion of the first electrode 101 away from the third electrode 109. Therefore, the portion of the first electrode 101 close to the third electrode 109 is higher in activity than the portion of the first electrode 101 away from the third electrode 109. Thus, a portion of the first pump cell 83 close to the third electrode 109 mainly pumps out oxygen from the first measurement chamber 89 to the element external space and pumps oxygen into the first measurement chamber 89 from the element external space. As a result, the first pump cell 83 has responsiveness to changes in the voltage Vs.

(1B) The NOx sensor 1 has the heater 65. The heater 65 is in contact with the element section 63. The heater 65 can effectively transfer heat to the element section 63 through heat conduction. Therefore, the NOx sensor 1 allows efficient performance of the rich aging treatment.

(1C) As shown in FIG. 3, in the NOx sensor 1, the heater 65, the reference cell 85, and the first pump cell 83 are stacked in the stacking direction. The stacking direction is the vertical direction in FIG. 3. The reference cell 85 is disposed between the heater 65 and the first pump cell 83 in the stacking direction. Therefore, even in the case where the heater 65 is used, an increase in the temperature of the first pump cell 83 can be suppressed. As a result, sublimation or property modification of the first electrode 101 can be suppressed.

Second Embodiment

1. Difference from First Embodiment

Since the basic structure of a second embodiment is identical with that of the first embodiment, the difference between the first embodiment and the second embodiment will be described. Notably, the same reference numerals as those used in the first embodiment denote the same structural elements, and their descriptions in the first embodiment will be referred to.

In the above-described first embodiment, the third electrode 109 is formed on the second solid electrolyte body 73. In contrast, in the second embodiment, the third electrode 109 is formed on the first solid electrolyte body 69 and is exposed to the first measurement chamber 89. The position of the third electrode 109 is rightward of the first electrode 101 in FIG. 3. The third electrode 109 faces the second electrode 99, with the first solid electrolyte body 69 intervening therebetween.

In the above-described first embodiment, the second solid electrolyte body 73, the third electrode 109 formed on the second solid electrolyte body 73, and the fourth electrode 111 correspond to the reference cell appearing in the claims. In contrast, in the second embodiment, the first solid electrolyte body 69, the third electrode 109 formed on the first solid electrolyte body 69 as described above, and the second electrode 99 correspond to the reference cell appearing in the claims. In the second embodiment, the second electrode 99 corresponds to the pump cell second electrode and the reference cell second electrode appearing in the claims, and the third electrode 109 formed on the first solid electrolyte body 69 corresponds to the reference cell first electrode appearing in the claims.

In the second embodiment, the pump cell solid electrolyte body and the reference cell solid electrolyte body are united into a single body. In the second embodiment, the pump cell second electrode and the reference cell second electrode are united into a single electrode.

In the above-described first embodiment, the reference oxygen chamber 113 corresponds to the reference space appearing in the claims and holding an atmosphere having a predetermined oxygen concentration. In contrast, in the second embodiment, the element external space to which the second electrode 99 is exposed corresponds to the reference space appearing in the claims and holding an atmosphere having a predetermined oxygen concentration. In the second embodiment, the space communicating with the element external space holds the same atmosphere as the reference space holding an atmosphere having a predetermined oxygen concentration.

2. Effects Achieved by NOx Sensor 1

The NOx sensor 1 of the second embodiment having been described in detail achieves the same effects as those achieved by the above-described NOx sensor 1 of the first embodiment.

Other Embodiments

The embodiments of the present disclosure have been described; however, the present disclosure is not limited to the above-described embodiments, and various modifications are possible.

(1) The sensor of the present disclosure may be a sensor other than an NOx sensor. For example, the sensor of the present disclosure may be a sensor obtained by removing the second pump cell 87 from the above-described NOx sensor 1. This sensor can measure the oxygen concentration in the gas under measurement on the basis of the current Ip1.

(2) The ceramic material contained in the first solid electrolyte body 69 and the first electrode 101 may be other than zirconia. Examples of ceramic materials other than zirconia includes $CeO_2$ (ceria), $ThO_2$ (thoria), $HfO_2$, and $Bi_2O_3$. The noble metal contained in the first electrode 101 may be other than platinum.

(3) A member which is not formed on the first solid electrolyte body 69 may be present on the outer circumferential side of the first electrode 101.

(4) In the first embodiment, the reference cell 85 may generate current in accordance with the difference between the oxygen concentration in the first measurement chamber 89 and the oxygen concentration in the reference oxygen chamber 113. In the NOx sensor 1, the current Ip supplied to the first pump cell 83 can be feedback-controlled such that that current becomes constant.

In the second embodiment, the reference cell 85 may generate current in accordance with the difference between the oxygen concentration in the first measurement chamber 89 and the oxygen concentration in the element external space. In the NOx sensor 1, the current Ip supplied to the first pump cell 83 can be feedback-controlled such that the current becomes constant.

(5) In the first and second embodiments, the space to which the second electrode 99 is exposed and which communicates with the element external space may be a flow channel, a chamber, or the like which communicates with the element external space.

(6) In the first embodiment, each of the first solid electrolyte body 69, the second solid electrolyte body 73, and the third solid electrolyte body 77 has the form of a single sheet. However, each of the first solid electrolyte body 69, the second solid electrolyte body 73, and the third solid electrolyte body 77 may be disposed in a through hole of a sheet-shaped insulating layer.

(7) The function of one constituent element in the above embodiments may be distributed to a plurality of constituent elements, or the functions of a plurality of constituent elements may be realized by one constituent element. Part of the configurations of the above embodiments may be omitted. Also, at least part of the configuration of each of the above embodiments may be added to or partially replace the configurations of other embodiments. Notably, all modes included in the technical idea specified by the wording of the claims are embodiments of the present disclosure.

(8) The present disclosure may be realized in various forms other than the above-described NOx sensor. For example, the present disclosure may be realized as a system which includes the NOx sensor as a structural element.

DESCRIPTION OF REFERENCE NUMERALS

1 . . . NOx sensor, 7 . . . gas sensor element, 65 . . . heater, 67, 71, 75, 79, 81 . . . insulating layer, 69 . . . first solid electrolyte body, 73 . . . second solid electrolyte body, 77 . . . third solid electrolyte body, 83 . . . first pump cell, 85 . . . reference cell, 87 . . . second pump cell, 89 . . . first measurement chamber, 91 . . . first diffusion resistor portion, 93 . . . second diffusion resistor portion, 95 . . . second measurement chamber, 97 . . . resistance heating element, 99 . . . second electrode, 101 . . . first electrode, 103 . . . opening, 105 . . . porous layer, 109 . . . third electrode, 111 . . . fourth electrode, 113 . . . reference oxygen chamber, 115 . . . fifth electrode, 117 . . . sixth electrode, 301 . . . A region, 303 . . . B region, 305 . . . farthest portion, 307 . . . closest portion, 309 . . . a-point, 313 . . . b-point

The invention claimed is:

1. A sensor comprising:
a detection section including a measurement chamber into which a gas under measurement is introduced;
a pump cell which pumps out oxygen from the measurement chamber to an element external space or pumps oxygen into the measurement chamber from the element external space; and
a reference cell which generates voltage Vs or current in accordance with the difference in oxygen concentration between the measurement chamber and a reference space which holds an atmosphere having a predetermined oxygen concentration, wherein
the pump cell includes a pump cell solid electrolyte body containing a ceramic material, a porous pump cell first electrode formed on the pump cell solid electrolyte body and exposed to the measurement chamber, and a pump cell second electrode formed on the pump cell solid electrolyte body and exposed to the element external space or a space communicating with the element external space,
the reference cell includes a reference cell solid electrolyte body, a reference cell first electrode formed on the reference cell solid electrolyte body and exposed to the measurement chamber, and a reference cell second electrode formed on the reference cell solid electrolyte body and exposed to the reference space,
the pump cell first electrode contains a noble metal and a ceramic material which is the same type of material as the ceramic material contained in the pump cell solid electrolyte body,
on a surface of the pump cell first electrode that is exposed to the measurement chamber, the pump cell first electrode includes a noble metal region formed of the noble metal, a ceramic region formed of the ceramic material, and a coexistence region where the noble metal and the ceramic material coexist,
the coexistence region in an A region of the surface has a width greater than that of the coexistence region in a B region of the surface,
the surface has a farthest portion farthest from the reference cell first electrode and a closest portion closest to the reference cell first electrode, the distance between the farthest portion and the closest portion being denoted by L,
the A region is a region within a circle whose center is located at an a-point on the surface offset from the closest portion toward the farthest portion by L/6 and whose radius is L/12, and
the B region is a region within a circle whose center is located at a b-point on the surface offset from the farthest portion toward closest portion the by L/6 and whose radius is L/12.

2. The sensor according to claim 1, further comprising a heater having a heating section, in which a heating element is embedded, wherein
the heating section is in contact with the detection section.

3. The sensor according to claim 2, wherein
the heater, the reference cell, and the pump cell are stacked in a stacking direction, and
the reference cell is disposed between the heater and the pump cell in the stacking direction.

4. The sensor according to claim 1, wherein the width of the coexistence region in the A region is equal to or greater than 1.1 times the width of the coexistence region in the B region.

5. The sensor according to claim 1, wherein
the pump cell solid electrolyte body and the reference cell solid electrolyte body are separate bodies,
the pump cell second electrode and the reference cell second electrode are separate electrodes, and
the reference space is a reference oxygen chamber which holds an atmosphere having a predetermined oxygen concentration.

6. A method of manufacturing a sensor comprising a detection section including a measurement chamber into which a gas under measurement is introduced, a pump cell which pumps out oxygen from the measurement chamber to an element external space or pumps oxygen into the measurement chamber from the element external space, a reference cell which generates voltage Vs or current in accordance with the difference in oxygen concentration between the measurement chamber and a reference space which holds an atmosphere having a predetermined oxygen concentration, and a heating section that is in contact with the detection section,
the pump cell including a pump cell solid electrolyte body, a porous pump cell first electrode formed on the pump cell solid electrolyte body and exposed to the measurement chamber, and a pump cell second electrode formed on the pump cell solid electrolyte body and exposed to the element external space or a space communicating with the element external space, the reference cell including a reference cell solid electrolyte body, a reference cell first electrode formed on the reference cell solid electrolyte body and exposed to the measurement chamber, and a reference cell second electrode formed on the reference cell solid electrolyte body and exposed to the reference space, the method comprising the step of performing rich aging treatment for the pump cell first electrode in which a temperature of the pump cell first electrode in an A region of a surface of the pump cell first electrode becomes higher than a temperature of the pump cell first electrode in a B region of the surface, wherein the heating section is provided in the sensor such that a difference in the temperature of the pump cell first electrode is realized between the A region and the B region, the surface has a farthest portion farthest from the reference cell first electrode and a closest portion closest to the reference cell first electrode, the distance between the farthest portion and the closest portion being denoted by L, the A region is a region within a circle whose center is located at an a-point on the surface offset from the closest portion toward the farthest portion by L/6 and whose radius is L/12, and the B region is a region within a circle whose center is located at a b-point on the surface offset from the farthest portion toward closest portion the by L/6 and whose radius is L/12.

7. The method of manufacturing a sensor according to claim 6, wherein the pump cell solid electrolyte body and the reference cell solid electrolyte body are separate bodies, the pump cell second electrode and the reference cell second electrode are separate electrodes, and the reference space is a reference oxygen chamber which holds an atmosphere having a predetermined oxygen concentration.

* * * * *